(12) United States Patent
Adair et al.

(10) Patent No.: US 7,670,566 B2
(45) Date of Patent: Mar. 2, 2010

(54) AIR TREATMENT DEVICES WITH USE-UP INDICATORS

(75) Inventors: Joel E. Adair, Racine, WI (US); Brian T. Davis, Burlington, WI (US); Gopal P. Ananth, Racine, WI (US); Thomas J. Szymczak, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1064 days.

(21) Appl. No.: 11/346,697

(22) Filed: Feb. 3, 2006

(65) Prior Publication Data

US 2007/0183932 A1 Aug. 9, 2007

(51) Int. Cl.
*A61L 9/01* (2006.01)
*A61L 9/02* (2006.01)
*A61L 9/03* (2006.01)

(52) U.S. Cl. ............... 422/125; 422/123; 422/124; 392/390; 392/391; 392/392; 392/393; 392/394; 392/403; 392/405; 43/129; 514/957; 239/34; 239/35

(58) Field of Classification Search ......... 422/123–125; 392/390–394, 403, 405; 239/34, 35; 43/129; 514/957

See application file for complete search history.

(56) References Cited

U.S. PATENT DOCUMENTS

| 3,999,946 | A | | 12/1976 | Patel et al. | |
|---|---|---|---|---|---|
| 4,128,508 | A | | 12/1978 | Munden | |
| 4,824,827 | A | | 4/1989 | Kelly et al. | |
| 4,921,636 | A | | 5/1990 | Traas | |
| 5,111,477 | A | | 5/1992 | Muderlak | |
| 5,269,460 | A | * | 12/1993 | Hautmann | ............... 239/35 |
| 5,647,052 | A | | 7/1997 | Patel | |
| 6,031,967 | A | | 2/2000 | Flashinski et al. | |
| 6,165,234 | A | * | 12/2000 | Kanakkanatt | ............... 44/275 |
| 6,348,627 | B1 | * | 2/2002 | Ross et al. | ............... 564/165 |
| 6,663,838 | B1 | | 12/2003 | Soller | |
| 6,790,670 | B2 | | 9/2004 | Munagavalasa et al. | |
| 2003/0152483 | A1 | | 8/2003 | Munagavalasa et al. | |
| 2004/0000087 | A1 | * | 1/2004 | Geyer et al. | ............... 43/125 |
| 2004/0045495 | A1 | * | 3/2004 | Yamasaki et al. | ............ 116/207 |
| 2004/0151747 | A1 | * | 8/2004 | Davis et al. | ............... 424/405 |
| 2005/0284952 | A1 | | 12/2005 | Davis et al. | |

FOREIGN PATENT DOCUMENTS

| EP | 1356731 A | 10/2003 |
|---|---|---|
| EP | 1418411 A | 12/2004 |
| GB | 2397022 A | 7/2004 |
| WO | 2004068945 A | 8/2004 |

OTHER PUBLICATIONS

International Search Report & Written Opinion for Application No. PCT/US2007/002903 dated Jan. 1, 2007.

* cited by examiner

*Primary Examiner*—Jill Warden
*Assistant Examiner*—Paul S Hyun

(57) ABSTRACT

Disclosed are devices for dispensing air treatment chemicals. There is a substrate bearing a first volatile air treatment chemical that is capable of being dispensed from the substrate when the substrate is heated, and an indicator unit holding a volatile indicator chemical separate from the first volatile air treatment chemical such that the volatile indicator chemical is capable of being dispensed from the unit when the unit is heated. The extent of dispensing of the first volatile air treatment chemical can be indicated by a visible cue whose appearance results from the dispensing of the volatile indicator chemical. In one form the unit also holds a second air treatment chemical. In another the indicator unit is a replaceable cartridge positionable more remote from the heater than the substrate.

14 Claims, 4 Drawing Sheets

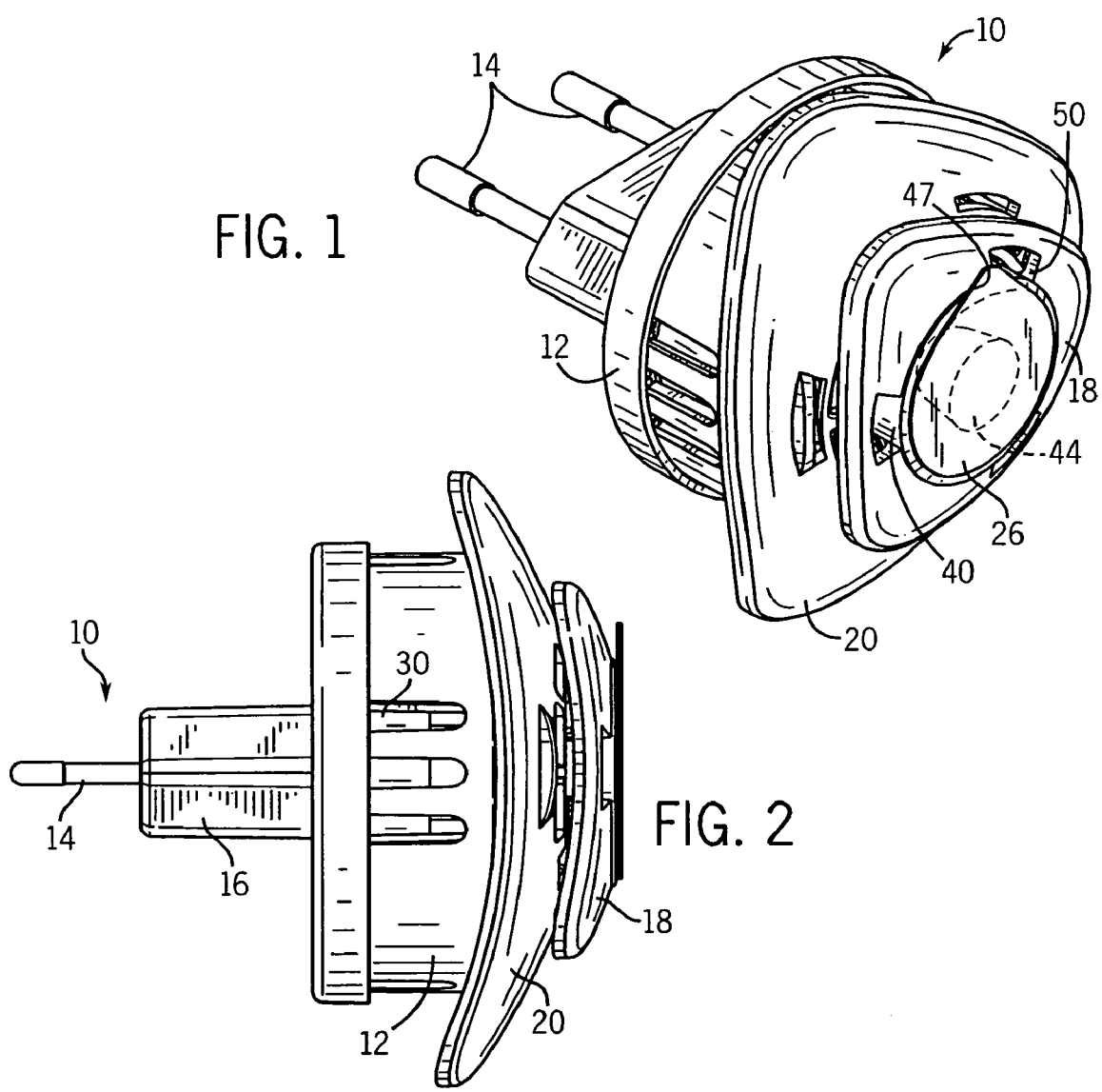
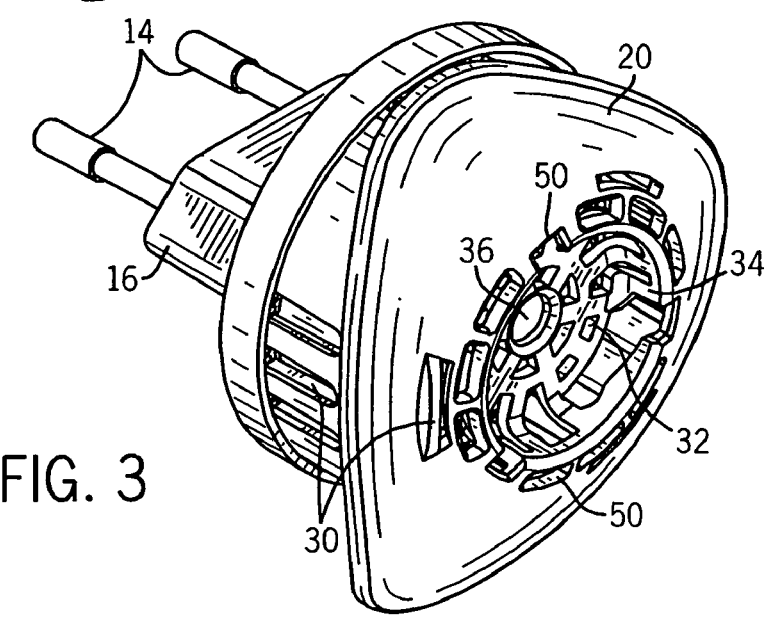

AIR TREATMENT DEVICES WITH USE-UP INDICATORS

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to devices that dispense a volatile air treatment chemical by heating a substrate impregnated with, or coated with, the chemical. More particularly it relates to indicators used with such devices to indicate when the treatment chemical has been used up.

Substrates (particularly porous substrates) have previously been used as carriers for air treatment chemicals such as insect control agents (insecticides, insect repellents, insect growth regulators, insect attractants, synergists, etc.), fragrances and deodorizers. See e.g. U.S. Pat. Nos. 5,111,477; 5,647,052 and 6,663,838. The disclosure of these patents, and of all other patents referred to herein, are incorporated by reference as if fully set forth herein.

Upon heating the substrate a volatile air treatment chemical is caused to be dispensed from the substrate. The heating source is typically an electrical heater, but may instead be a flame.

A variety of air treating functions can be achieved with such devices. For example, a porous substrate impregnated with volatile insecticide can be used to prevent mosquito biting in a confined bedroom. Alternatively, a deodorizing or desired odor or odor control material can be dispensed to overcome malodors or to provide a desired fragrance.

A disadvantage associated with such devices is that the consumer may not be aware of when the substrate has been exhausted. Unlike systems that have a wick extending into a visible reservoir, substrate-type systems often do not visibly change significantly as the active chemical is dispensed.

While it is possible to include a suggested useful life on the packaging for such products, consumers may not read or remember that information. Further, given the wide range of heater performance to which such substrates may be exposed, providing suggested useful life information may not be accurate. This can lead to use of the substrate after its effective useful life (with resulting consumer dissatisfaction). Alternatively, it can lead to premature disposal of a still useful substrate (and thus unnecessary cost and waste).

Hence, there have been efforts to better inform consumers regarding the extent of use-up of such substrates. Some such efforts use a chemical indicator that undergoes a visual change as the substrate is heated. See e.g. U.S. Pat. No. 4,128,508 (evaporation of an air treatment chemical causes a pH change and thus a color change); U.S. Pat. No. 4,824,917 (evaporation of a solvent leads to a color change); and U.S. Pat. No. 6,790,670 (evaporation of a dye leads to a color change).

However, this typically involved mixing a chemical needed for the indicator to work directly with the air treatment chemical. Care therefore needed to be taken to avoid selecting incompatible chemicals. Also, an indicator chemical could affect the volatization properties of the air treatment chemical. Further, coordinating the visual cue provided by the volatization of the indicator chemical with the rate of use of the air treatment chemical was difficult, particularly because both the indicator and the treatment chemical were being exposed to similar conditions, even though they might have different dispensing properties.

In U.S. Pat. Nos. 5,647,502 (limited duration bulb) and 6,663,838 (consumable candle) there was some discussion of coordinating the disappearance or destruction of a separate mechanical element with the useful life of the air treatment chemical. For example, when a candle that was one such heating device was used up, that also provided an indication that the substrate needed to be replaced. However, the candle system is not applicable to non-flame environments, and the use of limited duration bulbs can be relatively expensive.

In U.S. Pat. No. 4,921,636 there was a further teaching of a separately manufactured visual indicator that could be associated with an air treatment product. However, structures for using this concept were not described in detail in this patent, nor were ways of creating a joint replaceable cartridge using these features, nor were ways of positioning the indicator at a different distance from the heater than the air treatment chemical, nor were ways of providing additional air treatment functionality.

Thus, a need exists for improved air treatment devices with an automatic use-up indicator.

BRIEF SUMMARY OF THE INVENTION

In one aspect the invention provides an air treatment chemical dispensing system that has a substrate bearing a volatile air treatment chemical capable of being dispensed from the substrate when the substrate is heated, and an indicator unit holding a volatile indicator chemical separate from the air treatment chemical. The indicator chemical is capable of being dispensed from the unit when the unit is heated.

The system is configured such that the extent of dispensing of the air treatment chemical is indicated by a visible cue whose appearance results from the dispensing of the indicator chemical. The substrate and indicator unit are both preferably mounted on a single replaceable cartridge unit such that both the substrate and the indicator unit can be replaced simultaneously.

The visible cue can in part include a color change. Alternatively, it can merely be the visible disappearance of an amount of the indicator chemical.

There may also be a visible thermochromic dye associated with the indicator unit that changes color when heated. The thermochromic dye changes from a first color to a second color when first heated, and then returns to the first color upon subsequent cooling. This provides a visible off/on/off cue.

The substrate is preferably a porous, sand substrate impregnated with a volatile air treatment chemical selected from the group consisting of insect control agents, fragrances and deodorizers. For example, the air treatment chemical can be an insecticide such as a pyrethroid insecticide (e.g. transfluthrin), either provided neat or carried in a hydrocarbon or other solvent (such as Exxon Corporation's ISOPAR V™), where that formulation impregnates a substrate made of sand and resin binder.

The indicator unit is preferably a cup-shaped well holding the volatile indicator chemical, with a peel-off lid covering the well. In a preferred version the lid can have a permeable membrane positioned below the lid such that indicator operation is initiated by removing the peel-off cover because this permits volatile indicator chemical to diffuse through the permeable layer.

Most preferably the indicator unit comprises a transparent or at least translucent material that houses an indicator chemical. If the volatile indicator chemical is in the form of a gel, the disappearance of the gel through the permeable membrane (as the gel volatizes) can serve as the use-up indicator function. This is facilitated by making the walls of a well holding the gel transparent or translucent.

U.S. Pat. No. 6,031,967 generally describes units designed to permit dispensing air treatment chemicals from an internal well upon heating after removal of a peel-off lid cover. The well can be made from a heat-resistant plastic such as polyethylene terephthalate, and be provided with an integral surrounding upper flange. In the present invention, the lid can be a laminate whose outer layers are suitable to receive advertising and use information, and provide long term sealing. The inner layers (which are separable from the outer layers) can provide the permeable layer structure. One possible lid would have an outer polyester layer, under which is positioned a low density polyethylene layer, under which is positioned an aluminum foil layer, under which is positioned polypropylene, under which is positioned low density polyethylene material.

In another form of the invention there can also be a heater positioned proximate to the substrate and more remote from the indicator unit than the substrate. This form is particularly of interest where it is desired to slow the volatization rate of the indicator chemical somewhat to better coordinate it with the dispensing from the substrate, or where the indicator chemical is more heat sensitive.

In still another form of the invention the indicator unit also holds a second air treatment chemical that is capable of being dispensed from the unit when the unit is heated. For example, the first volatile air treatment chemical could be an insecticide and the second volatile air treatment chemical could be a synergist such as piperonyl butoxide that facilitates the insecticidal activity of the first volatile air treatment chemical. Alternatively, the second volatile air treatment chemical could be a fragrance.

Systems of the present invention are particularly of interest where the two volatile air treatment chemicals are incompatible for long term storage (if mixed together prior to storage). This could be because the two chemicals adversely react with each other, or because the optimal storage environments for each are not the same.

When using devices of the present invention, one preferably plugs the device into an electrical power source so as to cause a heater then linked to the electrical power source to heat the substrate and indicator unit. Simultaneously, one can remove the peel-off lid from the indicator unit, exposing the permeable membrane covering the indicator chemical. As a result, both the air treatment chemical and the indicator chemical can dispense into the surrounding environment. Optionally, at this time a thermochromic dye may also change color to indicate that the device is operating, and a second volatile air treatment chemical may begin to dispense as well.

When the indicator unit indicates the first volatile air treatment chemical has been completely used (e.g. the volatizing gel has completely disappeared), the substrate (and preferably a substrate/indicator unit combination) can be replaced. The heater apparatus is preferably retained for further use with replacement substrate and indicator units.

The substrate and indicator unit can be simultaneously replaced when they are both mounted on a cartridge unit. The cost of producing these devices is surprisingly low. These devices are reliable and effective for a variety of air treatment purposes.

The foregoing and other advantages of the present invention will be apparent from the following description. In the description that follows reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

BRIEF DESCRIPTION OF THE DRAWINGS

FIG. 1 is a frontal, lower perspective view of an air treatment device of the present invention;

FIG. 2 is a bottom plan view thereof;

FIG. 3 is a view similar to FIG. 1 but with a cartridge unit (bearing the substrate and the indicator unit) removed therefrom;

DETAILED DESCRIPTION OF THE PREFERRED EMBODIMENTS

Figure 4:
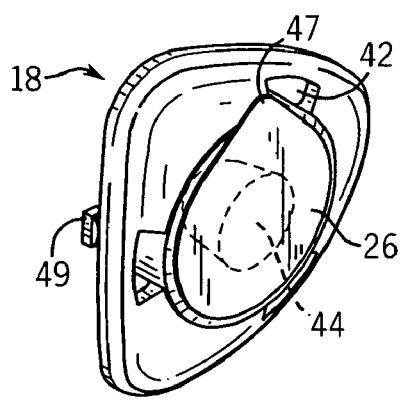
FIG. 4 is a view taken from the FIG. 1 perspective, but just of the cartridge unit.

Referring first to FIGS. 1-3, a preferred embodiment of an air treatment chemical dispensing device 10 of the present invention is shown. The device 10 has a housing 12 having electrical prongs 14 at a rear end 16 and a cartridge unit 18 at an opposing forward end 20. The device is most preferably plugged into an electric socket on a vertical wall. Hence, the directional terms in this patent are used with that type of installation in mind.

However, appropriate electric sockets on horizontal or other surfaces may also be used to provide power. Thus, the terms such as "front", "rear", "upper", "lower", and "side" should be interpreted in an analogous manner when the devices are used for that type of installation.

It should be noted that the prongs 14 shown in the figures are merely for purposes of example. Cylindrical prongs of this type are suitable for linking to electric power in some countries. However, in other countries blade prongs, or mixtures of blades, cylinders and other shaped prong elements will be used to supply the linkage to the available power (as is well recognized in the art).

Figure 9:
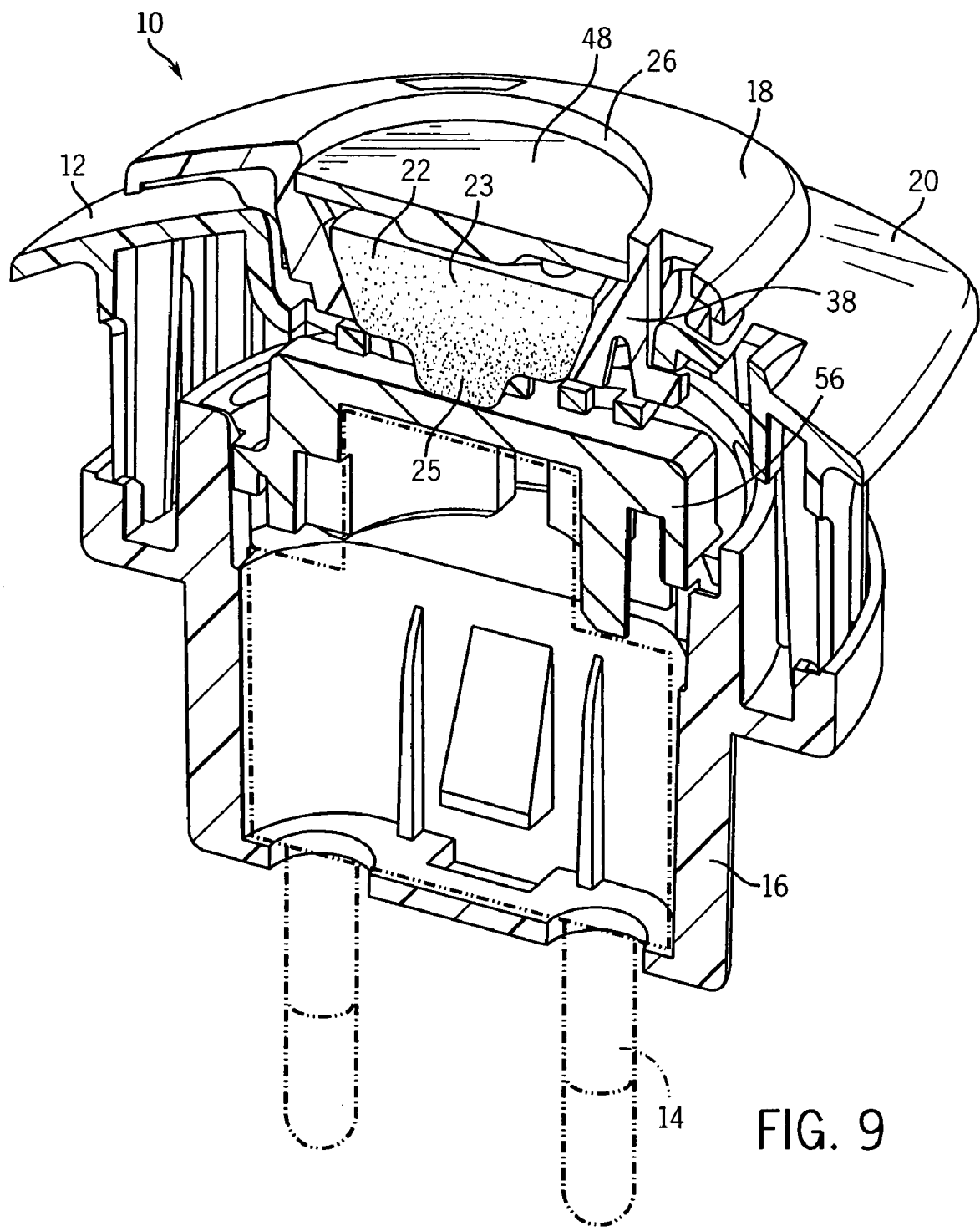
FIG. 9 is a sectional view of the FIG. 1 structure, albeit with the indicator button 26 removed.
Figure 10:
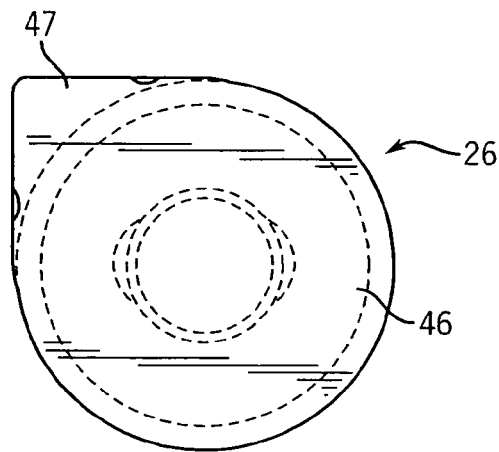
FIG. 10 is a front elevational view of the preferred indicator unit.

As is evident from FIG. 9, the preferred cartridge unit 18 has a substrate 22 having a forward frustum shaped section 23 and a rearward projecting nose 25. The substrate is impregnated with a volatile air treatment chemical capable of being dispensed from the substrate 22 when the substrate 22 is heated. As an alternative to being completely impregnated with the air treatment chemical, the substrate 22 may instead be only partially impregnated, or instead merely be coated with that chemical. In any event, the device is such that the extent of dispensing of that air treatment chemical will be indicated by a visible cue whose appearance results from the dispensing of an indicator chemical 28 associated with an indicator unit 26.

Figure 5:
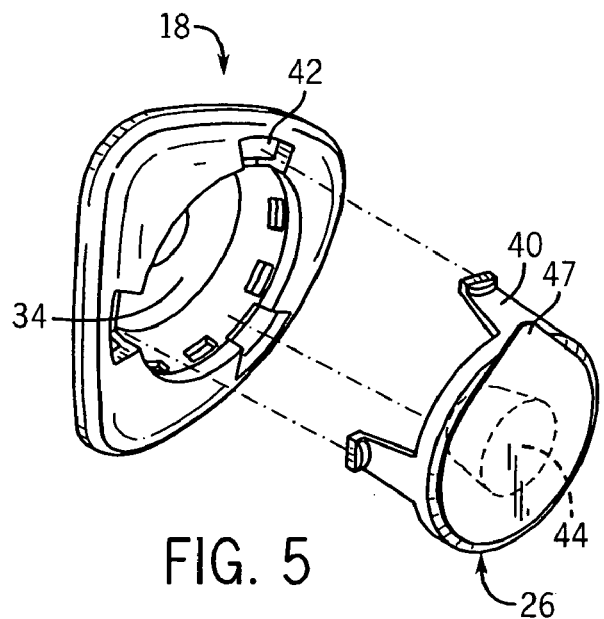
FIG. 5 is a view similar to FIG. 4, but with an indicator button exploded out from the cartridge unit.
Figure 6:
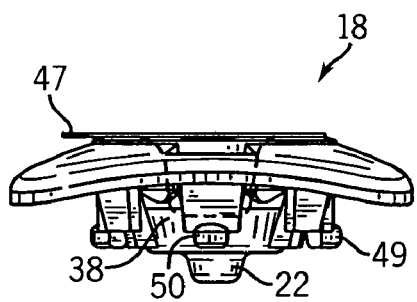
FIG. 6 is a bottom plan view of the cartridge unit.
Figure 7:
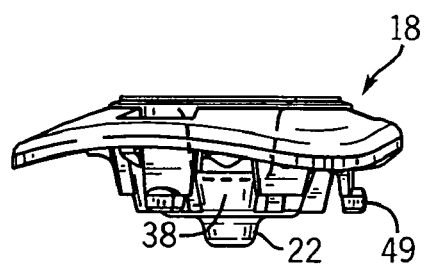
FIG. 7 is a side elevational view of the cartridge unit.
Figure 8:
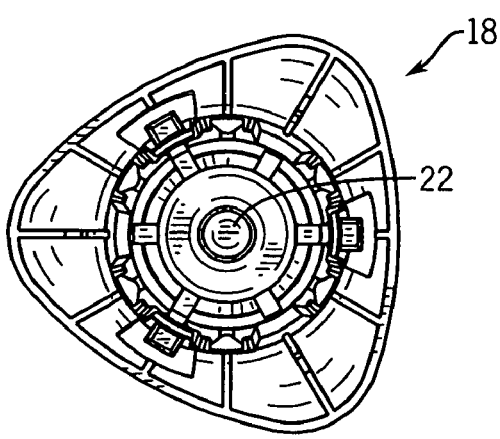
FIG. 8 is a rear elevational view of the cartridge unit.
Figure 11:
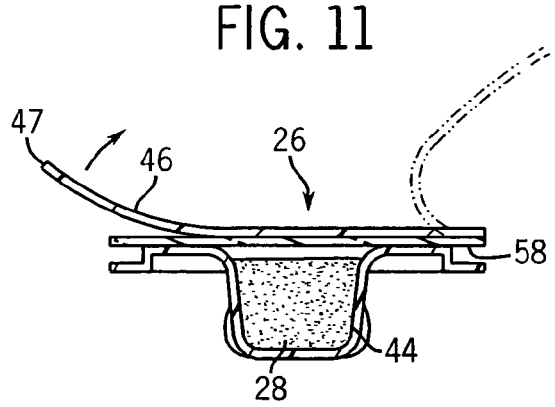
FIG. 11 is a partial sectional view thereof, showing the peel-off lid in the process of being removed.

As shown in FIGS. 5 and 11 (but not FIG. 9), indicator unit 26 is shown as holding a volatile indicator chemical 28 separate from the substrate 22. The indicator chemical is also capable of being dispensed when heated.

The main housing 12 of the overall device preferably encloses a heating element 56 such that the heating element is positioned proximal to a rearward end of the cartridge unit 18. The heating element is preferably activated by inserting the electrical prongs 14 into an outlet (not shown).

The housing 12 has a series of elongated vents 30 on the upper and lower sides of the housing 12. The vents 30 allow in air from the environment and permit it to pass along with the air treatment chemical dispensed from the substrate 22 through the vent openings on the upward side of the housing. It should be noted that the nose 25 of the substrate 22 is preferably positioned closely adjacent the heater with room around the nose for air to pass completely around its periphery.

Heat from the heating element 56 may also be permitted to pass against other surfaces of the cartridge unit 18 through a series of openings 32 and 36 as best seen in FIG. 3. Note however a separator panel 48 (as shown in FIG. 9) which provides some insulation to the indicator unit 26.

Referring next to FIGS. 4-8, the removable cartridge unit 18 has substrate 22 mounted to project through its rearward end and a separately installable indicator unit 26 mounted to project out from its forward end. In the most preferred form, there is a substantially circular cavity 38 (see FIG. 9) in the rearward center of the unit 18 which tapers rearwardly to hold the substrate 22). The particular shape of the substrate is not critical for purposes of this application, albeit the projecting nose 25 has certain advantages for quick start-up.

The indicator unit 26 is removable from the cartridge unit 18, thus allowing the indicator unit 26 and/or the substrate 22 to be separately replaced. Alternatively, the indicator chemical may be directly housed in a well of the cartridge unit 18.

The indicator unit 26 has a substantially circular (front view) unit having rear legs 40 symmetrically around the diameter of the unit 26. The legs 40 are preferably dimensioned and configured to releasably snap into corresponding slots 42 in the cartridge unit 18. Similarly, legs 49 of the cartridge unit permit quick attachment to the main device via corresponding grooves 50 in the housing 12 (via a bayonet type connection).

In a most preferred version (see e.g. FIGS. 10-14) a peel-off lid 46 is removable from the indicator unit 26, exposing the permeable membrane 58 covering the indicator chemical 28 to the environment (as the chemical may diffuse past the permeable membrane once the lid is removed). The lid has a tab section 47 to facilitate gripping of the peel-off lid. Once the lid is removed indicator operation is initiated because this allows the volatile indicator chemical 28 to escape to the environment upon heating.

In this configuration the indicator chemical is more remote from the heater than the substrate. Thus, it may be a chemical that is more volatile at a given temperature than the air treatment chemical which impregnates the substrate. Alternatively, the indicator chemical that is used may be a more heat-sensitive chemical.

In any event the indicator unit 26 may contain a second air treatment chemical in addition to the indicator chemical 28. The second volatile air treatment chemical may be combined with the indicator chemical 28 in the cup-shaped well 44.

Figure 13:
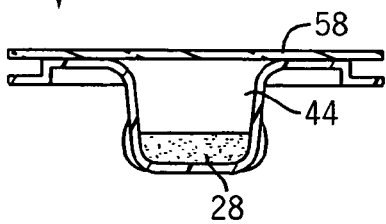
FIG. 13 is a view similar to FIG. 11, but after the peel-off lid has been removed and some of the indicator chemical has volatized.
Figure 12:
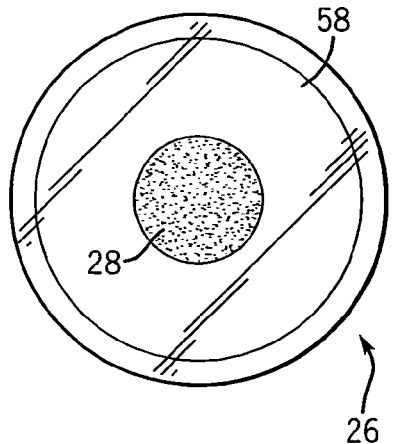
FIG. 12 is a frontal view of the FIG. 13 construction, albeit with the FIG. 11 level of indicator chemical shown.
Figure 14:
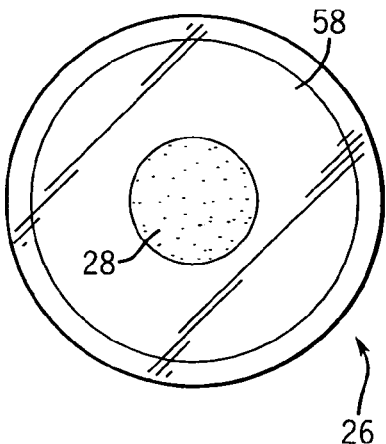
FIG. 14 is a frontal view similar to FIG. 12, but showing the indicator unit with the indicator chemical at the FIG. 13 level.

As the indicator chemical 28 is heated (and dispensed into the environment) a visible cue results in that one will be able to see (as shown in FIGS. 13 and 14) that the chemical is disappearing (or at some point has completely disappeared). When a consumer sees this they will know that the end of utility is near, and then know that the substrate 22 is essentially used up. By "use-up cue" we mean either that an extent of use is indicated, or that completion of use is indicated.

Where the indicator volatile is colored, a portion of the visible cue may be a color change. Moreover, a thermochromic dye (such as copper mercury iodide) may be added to the indicator volatile that changes color when heated. In a preferred version, the thermochromic dye changes from a first color to a second color when heated, and then returns to the first color upon subsequent cooling, to thereby provide a visible off/on/off cue.

When the first and/or second volatile air treatment chemical is an insecticide and/or insect repellent, organic phosphorous insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, PynaminR™, benfluthrin, bifenthrin, bioallethrin as Pynamin ForteR™, S-bioallethrin, esbiothrin, esbiol, bisoresmethrin, cyclopro-thrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, tau-fluvalinate, kadethrin, permethrin, phenothrin, prallethrin as EtocR™, resmethrin, tefluthrin, tetramethrin, tralomethrin, or transfluthrin. Other volatile insecticides, such as those described in U.S. Pat. No. 4,439,415, can also be employed.

In particularly preferred versions the volatile insecticide is selected from the group consisting of transfluthrin, metofluthrin, vapothrin, permethrin, prallethrin, tefluthrin and esbiothrin. Transfluthrin is the most preferred insecticide.

Possible solvents for carrying these air treatment chemicals include, but are not limited to, ISOPAR™ C, ISOPAR™ E, ISOPAR™ L, heptane, methanol, acetone, ethanol, isopropyl alcohol, dodecene and tetraydrofuran, ISOPAR™ C, ISOPAR™ E and ISOPAR™ L are hydrocarbon solvents of varying chain length and are available from Exxon Chemical Company, and are particularly preferred.

Typically, volatile insect control agents will be applied to a substrate in an organic solvent such as a hydrocarbon. One desirable impregnation formulation for mosquito control is 50% wt. transfluthrin dissolved in Exxon Corporation's ISO-PAR C hydrocarbon. Preferably, however, transfluthrin is applied to a suitable substrate without use of a solvent. The transfluthrin can be heated to about 60° C. and applied to a porous substrate, with the substrate heated to about 250° C.

A wide variety of volatile fragrances may be used which may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters.

When an volatile air treatment chemical is a disinfectant, preferred disinfectants include, but are not limited to, glycols, trimethylene and dipropylene. Organic acids compatible with the use of the substrate 22 and environment may also be used.

The substrate 22 can be fabricated from any material that is capable of absorbing the volatile air treatment chemical, remaining essentially stable under heating conditions, and releasing the air treatment chemical under heating conditions. Examples of a suitable substrate 22 include but are not limited to porous sand with a binder such as novolac resin, urethane resins and highly cross linked thermoplastics such as cross linked polyethylene. Particularly preferred sand substrates can be made in a fashion analogous to the sand wicks described in U.S. patent application publication 2005/0284952. Alternative substrates include cellulose, glass fiber filters, synthetic paper materials, ceramic materials, textiles, felt-type materials, wovens and nonwovens, bonded or sintered synthetics, natural polymer powders, and the like.

The indicator chemical 28 can be any material that provides a visual cue when exposed to heating that it is being heated. In a preferred version, the indicator chemical 28 is in the form of a liquid or, alternatively, a gel or other semi-solid material. Other fluid-based compounds may also be used.

Particularly preferred volatile indicator chemicals are those guaiazulene dye materials described in U.S. Pat. No. 6,790,670 (which is hereby incorporated by reference as if fully set forth herein). It should also be noted that this patent describes a variety of ways of more precisely controlling the speed of volatilization of such dyes (e.g. using retarders and solvents, among other means).

Apart from the preferred indicator system it should be understood that (as taught in U.S. Pat. No. 6,031,967) a wide variety of materials are known to slowly permeate out of a unit through a permeable membrane when heated. Such a device (even if containing a second air treatment chemical) could function as a visual use-up cue if the walls of that device were made transparent or translucent, so that a consumer could see the disappearance of that material.

While preferred embodiments of the present invention have been described above, it should be appreciated that the invention could be used in a variety of other embodiments. For example, it is not critical that the indicator well be mounted directly onto the removable cartridge that carries the substrate. In this regard, the substrate could be separately positioned on the heating device.

Thus, the principles of the present invention can be applied in a variety of other ways apart from those specifically noted herein and/or depicted in the drawings. Still other modifications may be made without departing from the spirit and scope of the invention. Thus, the claims (rather than just the preferred embodiments) should be reviewed in order to understand the full scope of the invention.

INDUSTRIAL APPLICABILITY

Disclosed are air treatment devices with improved visual use-up cue capabilities.

We claim:

1. An air treatment chemical dispensing system, comprising:
    a cartridge housing having a substrate mounted therein which has a first facing portion facing in a first direction, the substrate bearing a volatile air treatment chemical capable of being dispensed from the first facing portion when the substrate is heated, and
    an indicator unit mounted in the cartridge housing which has a second facing portion facing in a second direction that is opposed from said first direction, the indicator unit holding a volatile indicator chemical separate from the air treatment chemical such that the indicator chemical is capable of being dispensed from the second facing portion when the unit is heated;
    wherein the system is configured such that an extent of dispensing of the air treatment chemical is indicated by a visible cue whose appearance results from the dispensing of the indicator chemical.

2. The air treatment chemical dispensing system of claim 1, wherein the visible cue further comprises a color change.

3. The air treatment chemical dispensing system of claim 1, wherein the visible cue comprises the visible disappearance of an amount of volatile indicator chemical.

4. The air treatment chemical dispensing system of claim 1, further comprising a visible thermochromic dye that changes color when heated.

5. The air treatment chemical dispensing system of claim 4, wherein the visible thermochromic dye changes from a first color to a second color when heated, and then returns to the first color upon subsequent cooling, to thereby provide a visible off/on/off cue.

6. The air treatment chemical dispensing system of claim 1, wherein the substrate is a porous sand substrate.

7. The air treatment chemical dispensing system of claim 1, wherein the air treatment chemical is selected from the group consisting of insect control agents, fragrances, and deodorizers.

8. The air treatment chemical dispensing system of claim 1, wherein the indicator unit is in a form of a cup-shaped well holding the indicator chemical, the well being covered by a lid.

9. The air treatment chemical dispensing system of claim 8, wherein the lid has an outer peel-off cover with a permeable membrane positioned below the cover.

10. The air treatment chemical dispensing system of claim 8, wherein the volatile indicator chemical, when in the well, is in the form of a gel.

11. An air treatment chemical dispensing system, comprising:
    a cartridge housing having a substrate mounted therein which has a first facing portion facing in a first direction, the substrate bearing a first volatile air treatment chemical capable of being dispensed from the first facing portion when the substrate is heated, and
    an indicator unit mounted in the cartridge housing which has a second facing portion facing in a second direction that is opposed from said first direction, the indicator unit holding a volatile indicator chemical separate from the air treatment chemical such that the indicator chemical is capable of being dispensed from the second facing portion when the unit is heated;
    wherein the system is configured such that an extent of dispensing of the air treatment chemical is indicated by a visible cue whose appearance results from the dispensing of the indicator chemical; and
    wherein the indicator unit also holds a second volatile air treatment chemical capable of being dispensed from the unit when the unit is heated.

12. The air treatment chemical dispensing system of claim 11, wherein the second volatile air treatment chemical is selected from the group consisting of insect control agents, fragrances, and deodorizers.

13. The air treatment chemical dispensing system of claim 11, wherein the first volatile air treatment chemical is an insecticide and the second volatile air treatment chemical is a synergist that facilitates insecticidal activity of the first volatile air treatment chemical.

14. The air treatment chemical dispensing system of claim 11, wherein the first volatile air treatment chemical is an insect control agent and the second volatile air treatment chemical is a fragrance.

* * * * *